United States Patent [19]

Eliash

[11] Patent Number: 5,298,129

[45] Date of Patent: Mar. 29, 1994

[54] METHOD OF SELECTIVELY MONITORING TRACE CONSTITUENTS IN PLATING BATHS

[75] Inventor: Bruce M. Eliash, Los Angeles, Calif.

[73] Assignee: Hughes Aircraft Company, Los Angeles, Calif.

[21] Appl. No.: 976,118

[22] Filed: Nov. 13, 1992

[51] Int. Cl.⁵ ............................................ G01N 27/26
[52] U.S. Cl. .............................. 204/153.1; 204/412; 204/434
[58] Field of Search ..................... 204/412, 434, 153.1, 204/DIG. 8, DIG. 9; 205/81, 101, 102, 103, 104, 105

[56] References Cited

PUBLICATIONS

Tench, Cyclic Pulse Voltammetric Stripping Analysis of Acid Copper Plating Baths, Apr. 1985, pp. 831–834.

*Primary Examiner*—John Niebling
*Assistant Examiner*—Bruce F. Bell
*Attorney, Agent, or Firm*—M. E. Lachman; M. W. Sales; W. K. Denson-Low

[57] ABSTRACT

A method of selectively monitoring particular trace constituents within a plating bath containing multiple trace constituents. The method provides improved selectivity over known voltammetric techniques for certain plating baths and trace constituents. The method involves applying a brief voltammetric plating signal to a pretreated electrode positioned within the plating bath solution, applying a rapid stripping signal to the plated electrode, and monitoring the resultant stripping signal response current. The characteristics of the stripping signal response current indicate the particular trace constituent concentration level. The method complements and is easily integrated with known voltammetric techniques and equipment, and thus improves the efficiency and versatility of existing plating bath analysis systems.

11 Claims, 1 Drawing Sheet

METHOD OF SELECTIVELY MONITORING TRACE CONSTITUENTS IN PLATING BATHS

This invention was made with support provided by the United States Government under Contract Number DAAB07-88-C-A047 awarded by the Department of the Army. The U.S. Government has certain rights to this invention.

BACKGROUND OF THE INVENTION

1. Field of the Invention

The present invention relates generally to plating baths and methods for monitoring the trace constituents contained therein. More particularly, the method of the present invention relates to a voltammetric analysis technique that accurately and selectively indicates the level of a particular trace constituent in plating baths containing multiple trace constituents. The method can be used to maintain desired trace constituent concentrations in order to ensure optimal plating bath performance.

2. Description of Related Art

A typical plating bath solution is comprised of a combination of several distinct electrochemical constituents. The specific constituents vary depending upon the type of plating bath, but in general can be broadly divided into what are commonly known as major constituents and trace, or minor, constituents. The major constituents are those electrochemical constituents which make up about 2 to 25 percent of the total bath weight. Trace constituents, on the other hand, are present in smaller quantities, usually less than 0.5 percent of the total weight. Organic addition agents, degradation products and chemical contaminants are typical trace constituents.

Most plating baths contain several distinct trace constituents. Appropriate concentration levels of these trace constituents must be maintained in order to ensure a high quality deposit. Trace constituent concentrations influence certain important characteristics of the deposit, including tensile strength, ductility, solderability, uniformity, brightness and resistance to thermal shock.

In terms of organic addition agents, plating baths frequently contain throwing power enhancers, brighteners, grain refiners, ductility promoters and wetting agents. For example, a Lea Ronal acid cadmium plating bath may contain trace concentrations of the organic addition agents Starter K, Brightener KR, and Stabilizer. Each of these organic addition agents affects various qualities of the resultant plating deposit by adsorbing onto the plated surface.

Current techniques for monitoring the trace constituents of plating baths include real time voltammetric monitoring techniques such as those in U.S. Pat. No. 4,631,116, assigned to the present assignee. The method disclosed therein uses a voltammetric signal to produce ac current spectra which vary as a result of changes in the various trace constituent concentrations. Voltammetric methods such as these have been found to produce accurate results in real time for most trace constituents.

Although well-suited for their intended purpose, the above voltammetric techniques may not yield accurate results for all types of plating baths and the trace constituents contained therein. To ensure accurate measurements and a high quality plating deposit, it is important that the analysis technique adequately distinguish among the various trace constituents. The measurements should be unambiguous and highly selective. For certain plating bath trace constituents, the voltammetric techniques of U.S. Pat. No. 4,631,116 are insufficiently selective to permit optimal plating bath analysis. For example, in the Lea Ronal acid cadmium bath discussed above, first or second harmonic ac voltammetry does not adequately distinguish the various organic addition agent concentrations. Other voltammetric techniques, such as those disclosed in U.S. Pat. No. 4,132,605 and U.S. Pat. No. 4,812,210, are similarly limited in their ability to accurately monitor certain multiple trace constituents present in a single bath.

As is apparent from the above, there presently is a need for a method of selectively monitoring trace constituent concentrations within a plating bath containing certain multiple trace constituents. The method should provide accurate real-time results in situations where the accuracy of known multiple trace constituent analysis techniques is limited. Furthermore, the method should complement and be easily integrated with known voltammetric techniques and equipment, resulting in an efficient and flexible overall plating bath analysis system.

SUMMARY OF THE INVENTION

In accordance with the present invention a method for monitoring the concentration of trace constituents within a plating bath is disclosed. The method is particularly well suited for accurately monitoring the concentration level of a particular organic additive in a plating bath containing multiple organic additives. However, the method may also be used to distinguish other types of trace constituents in a multiple trace constituent plating bath. The present invention is based upon the discovery that by rapidly plating and stripping an additive-free electrode surface, a particular rapidly adsorbed trace constituent may be distinguished from other less rapidly adsorbed trace constituents in the same bath.

The method of the present invention involves the steps of providing a sensing electrode in contact with a plating bath solution containing multiple trace constituents, metal ions and a supporting electrolyte; applying a pretreatment signal to the electrode in order to remove additives and contaminants from its surface in preparation for subsequent plating and stripping; applying a brief plating signal to the pretreated electrode to plate a portion of the metal ions onto the electrode surface and to allow a portion of the particular trace constituent to be adsorbed on the electrode surface; applying a stripping signal to the electrode to strip off the plating from the electrode; and monitoring signal characteristics of the stripping signal response current in order to provide an indication of a particular trace constituent concentration.

In accordance with the present invention, one of the response current signal characteristics which may be monitored is the time required for this current to be reduced to zero. This time is not influenced by the presence of other, less rapidly adsorbed trace constituents. Thus, the time required to strip the plating deposit from the electrode surface can accurately indicate the concentration of the more rapidly adsorbed trace constituent.

As a feature of the present invention, the method is highly selective and can accurately distinguish a particular trace constituent in a plating bath containing multiple trace constituents. For example, the method will accurately determine the concentration level of the organic additive Starter K present in a typical acid cadmium plating bath containing other trace constituents. The method can also be used to monitor the concentration of a more rapidly adsorbed trace constituent in many other types of plating baths.

As another feature of the present invention, the method provides an accurate alternative analysis technique for those situations in which the selectivity of known real-time voltammetric techniques is limited. For example, the accuracy of the trace constituent monitoring techniques disclosed in U.S. Pat. No. 4,631,116 is limited in the case of the multiple organic addition agents present in a typical acid cadmium bath. The method of the present invention provides improved accuracy and selectivity in such situations. The method of the present invention thus serves to complement and extend the capabilities of existing voltammetric analysis techniques.

As a further feature of the present invention, the method is easily integrated with known trace constituent measurement methods and equipment, thereby providing an efficient and flexible overall plating bath analysis system suitable for accurately monitoring a wide variety of plating baths and their respective trace constituents. Since the present invention can be implemented using equipment suitable for other voltammetric techniques, only a single set of analysis equipment need be maintained.

As an additional feature of present invention, optimal signal parameters for monitoring the concentrations of multiple organic additives within a typical acid cadmium bath are disclosed. Furthermore, the method provides an experimental framework for determining optimal measurement signal parameters for selectively monitoring trace constituents in other types of plating baths.

The above-discussed features and attendant advantages of the present invention will become better understood by reference to the following detailed description and the accompanying drawings.

DESCRIPTION OF THE PREFERRED EMBODIMENTS

The present invention distinguishes a particular trace constituent from other trace constituents with different adsorption rates in a plating bath by rapidly plating and stripping a pretreated metal electrode. Monitoring the stripping signal response current characteristics can provide an accurate and highly selective indication of the concentration level of a particular trace constituent adsorbed on the electrode surface.

The present invention has wide application to many different plating baths and trace constituents. Although the following description applies the method of the present invention to an exemplary acid cadmium bath containing several organic addition agents as trace constituents, it should be understood that this is by way of example and not limitation. The method of the present invention can selectively distinguish among many other types of multiple trace constituents in a wide variety of different plating baths. The method is particularly well-suited for those situations in which the selectivity of other voltammetric techniques, such as those disclosed in U.S. Pat. No. 4,631,116, is limited.

Figure 1:
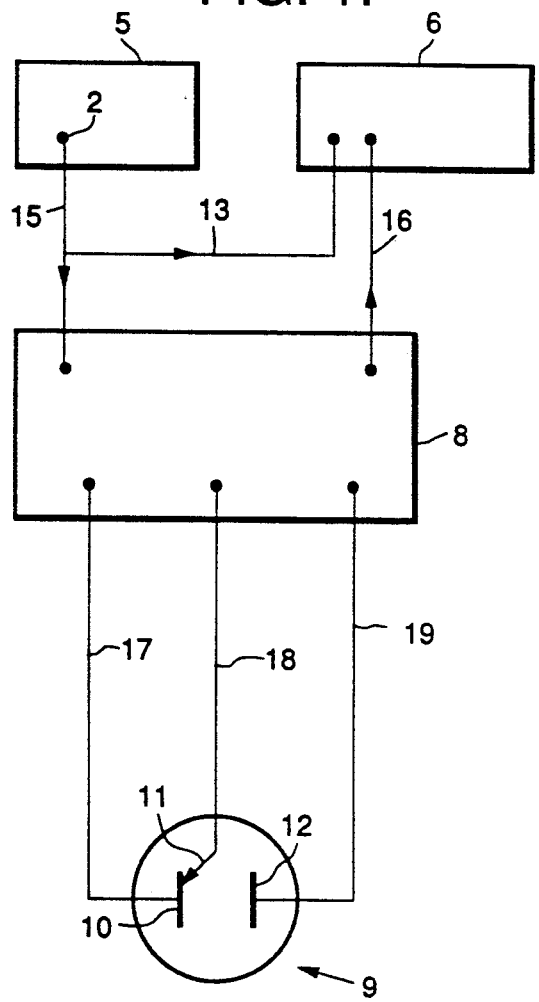
FIG. 1 is a schematic representation of a preferred exemplary system for conducting the method in accordance with the present invention.

The schematic diagram of FIG. 1 illustrates a preferred exemplary system for conducting the method of the present invention. It should be noted that the equipment of this system is readily compatible with the equipment used in conjunction with other voltammetric techniques. The present method therefore serves to extend the capability of the other voltammetric techniques without the need for additional equipment.

Figure 2:
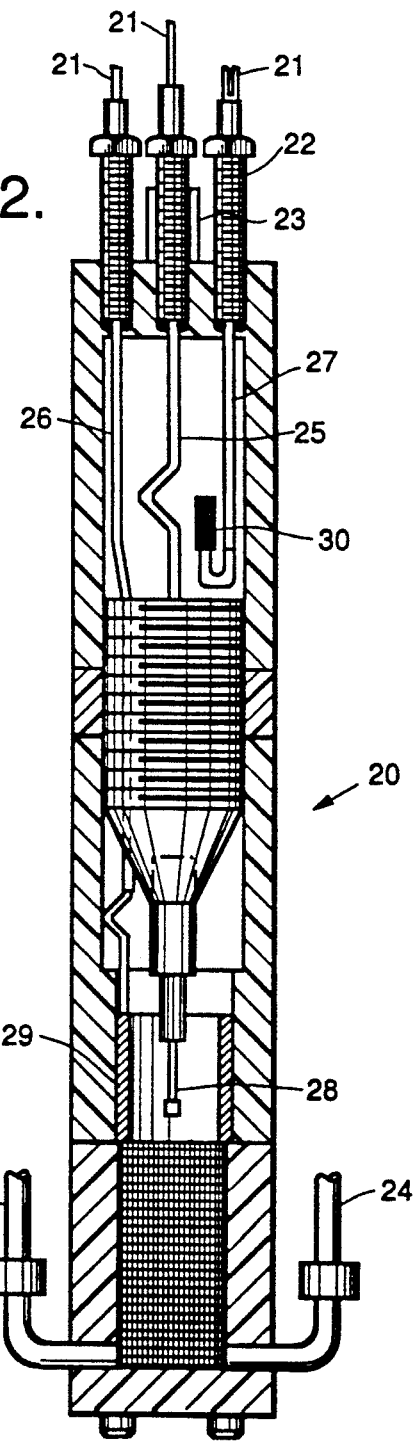
FIG. 2 is a detailed side sectional view of the exemplary electrochemical sensor which is shown schematically in FIG. 1.

In the exemplary system of FIG. 1, the plating bath solution is located within an electrochemical cell 9. The electrochemical cell 9 is preferably part of an electrochemical sensor submerged within the plating bath. One such exemplary in-tank sensor is shown in FIG. 2. The solution can be drawn into sensor 20 via inlets 24 by an external pump (not shown). The solution passes through the sensor 20 and back to the pump through outlet tube 23. Within the sensor 20, the solution is in contact with working electrode 28, counter electrode 29, and reference electrode 30. These electrodes are connected to the external wires 21 via leak-proof bushings 22 and insulated conductors 25, 26 and 27, respectively. The external wires 21 provide connections to the appropriate test equipment.

Referring again to the test equipment shown schematically in FIG. 1, the potentiostat 8 serves to generate an electrode pretreatment signal of appropriate amplitude and duration. The pretreatment signal removes any adsorbed organics or other contaminants from the electrode surface and otherwise prepares it for subsequent plating. Alternatively, the pretreatment signal could be supplied by the waveform generator 5.

The waveform generator 5 provides an output 15 which is an appropriate voltammetric signal waveform having a suitable amplitude and duration. The voltammetric signal is applied to the external input of potentiostat 8 and to the reference input of a display device 6. Alternatively, the voltammetric signal can be generated within the potentiostat itself. An exemplary potentiostat with internal signal generating capability is the PAR model 273 available from Princeton Applied Research, of Princeton, N.J. Display device 6 can include a digital data acquisition system, an oscilloscope or any other suitable display means. The potentiostat 8 further serves to ensure that the pretreatment and voltammetric signal amplitude remains constant despite variations in current flow through the electrochemical cell 9.

The pretreatment and voltammetric signals passing through or generated within potentiostat 8 are applied to the sensing electrode 10 in the electrochemical call 9 via line 17. The electrochemical cell 9 also contains a counter electrode 12 and a standard calomel or other suitable reference electrode 11. All system voltage measurements are taken relative to this reference electrode 11. The reference electrode 11 and counter electrode 12 are connected to the potentiostat 8 via lines 18, 19, respectively. This three-electrode electrochemical sensor design is suitable for use with many different voltammetric techniques.

When the voltammetric signal is applied to the pretreated sensing electrode 10, a response current is generated between the sensing electrode 10 and the counter electrode 12. The response current varies depending upon the electrochemical processes occurring at the surface of the sensing electrode 10. The electrochemical processes are a function of the trace constituent concentrations, and the response current is therefore indicative of these concentrations. The response current passes back through the potentiostat 8 and is monitored on display device 6. From the potentiostat output the response current is applied to the signal input of display device 6 via line 16. The response current displays represent unique spectra which indicate the trace constituent composition of the plating bath solution within the electrochemical cell.

In accordance with the present invention, the voltammetric equipment described above selectively determines a particular trace constituent concentration in the following manner. The pretreatment signal is applied to the sensing electrode 10 to remove addition agents and contaminants and prepare an additive free surface for subsequent plating. The voltammetric signal is then applied to the sensing electrode 10 to ascertain the concentration level of a particular trace constituent. The voltammetric signal consists of an appropriate plating signal waveform followed by an appropriate stripping signal waveform.

The method uses the variation in trace constituent diffusion and adsorption rates to measure concentration levels of particular trace constituents. For example, the most mobile trace constituent will be the first to reach an additive-free electrode surface. As the first adsorbed trace constituent on the surface, this particular trace constituent is the primary influence on the resultant electrode plating. A very brief plating signal is required to prevent other, less rapidly adsorbed trace constituents from influencing the plating deposit. In this manner, the method is able to isolate the effect of a single trace constituent from other trace constituents within the same plating bath solution. By then stripping the plated electrode, to determine the amount of material plated during the brief plating signal, the effect of the most rapidly adsorbed trace constituent on the plating deposit can be determined. This effect can be readily correlated to constituent concentration level by monitoring the stripping signal response current.

Although the above discussion is primarily directed to distinguishing the most rapidly adsorbed trace constituent, it should be understood that this is by way of example only. The method may also be used to distinguish the effects of other particular trace constituents which influence the plating deposit but are not necessarily the most rapidly adsorbed in the bath. For example, in certain baths the most rapidly adsorbed trace constituent may not influence the plating deposit, and its effect will therefore not be reflected in the stripping signal response current. In such a situation, the method could still be used to distinguish a different trace constituent from other less rapidly adsorbed constituents in the bath.

In order to optimize the accuracy of the stripping signal response current spectra produced in accordance with the present invention, it is necessary to vary a number of independent physical test parameters. These parameters include: 1) pretreatment signal amplitude and duration; 2) type of plating signal waveform; 3) plating signal amplitude and duration; 4) type of stripping signal waveform; 5) stripping signal amplitude and duration; and 6) stripping signal response current characteristic measured. These parameters were independently varied to determine the preferred system parameters for monitoring trace constituents using the preferred voltammetric system of FIG. 1. It should be noted, however, that alternative combinations of pretreatment, plating and stripping signal parameters may also produce similar measurement results.

In general, certain system parameters are particularly well-suited for selectively distinguishing individual trace constituent concentrations in multiple trace constituent plating baths. The following voltages are with respect to a saturated calomel electrode. The working electrode is preferably pretreated at an anodic potential of about 2.5 to 3.5 volts, for a period of about 5 to 15 seconds. Dc pulse waveforms are preferred for both the plating and stripping signals. A dc pulse signal with a potential sufficiently cathodic to produce an average current density of about 100 to 1000 ma/cm$^2$ and a duration of about 50 to 100 milliseconds (ms) is used as a plating signal, and a dc pulse signal with a voltage sufficiently cathodic to strip the plated metal deposit over a duration of about 5 to 1000 ms is used for the stripping signal. These pulse signals ensure that particular trace constituents within the plating bath can be distinguished on the basis of adsorption rates. For example, a rapid pulse signal can be used to permit only the most rapidly adsorbed trace constituent to influence the plating deposit. Other rapid signal waveforms could also be used for this purpose.

The selection of the proper plating signal duration is an important aspect of the method. A particular trace constituent with a relatively high adsorption rate will reach the electrode surface before other less rapidly adsorbed constituents, and may either accelerate or suppress the plating rate. The plating signal duration should be shorter than the time required to adsorb enough of the particular trace constituent to form a monolayer coverage saturating the electrode surface. Once a monolayer of the particular trace constituent saturates the electrode surface, the accuracy of the subsequent measurements will be impaired. When the electrode surface is properly plated, the response current produced by the stripping signal can be monitored by determining the time interval between initial application of the stripping signal response and the time at which the stripping signal response current is reduced to zero. Alternatively, other characteristics of the response current, such as the area of the stripping peak or the time to reach half of the stripping peak height, could be monitored. The time interval to reduce the current to zero can be readily correlated to the concentration level of the particular trace constituent.

An example of the optimization of the exemplary voltammetric system of FIG. 1 to the detection of a specific trace constituent in a multiple constituent bath is as follows. As previously discussed, a typical acid cadmium bath contains at least three organic addition agents as trace constituents. These constituents include, but are not limited, to Starter K (a Lea Ronal proprietary composition comprising ethoxylated surfactants), Brightener KR (a Lea Ronal proprietary composition to brighten the deposit), and Stabilizer (a Lea Ronal proprietary composition comprising alkylaryl thiourea derivatives including N,N'-diethylthiourea). Voltammetric techniques, such as those disclosed in U.S. Pat. No. 4,631,116 are unable to adequately distinguish among these constituents, and therefore cannot accurately measure the additive concentrations. The method of the present invention has been applied to an acid cadmium plating bath containing these three organic additives, which is available from Lea Ronal of Freeport, N.Y. as a Kadizid bright acid cadmium plating bath.

Figure 3:
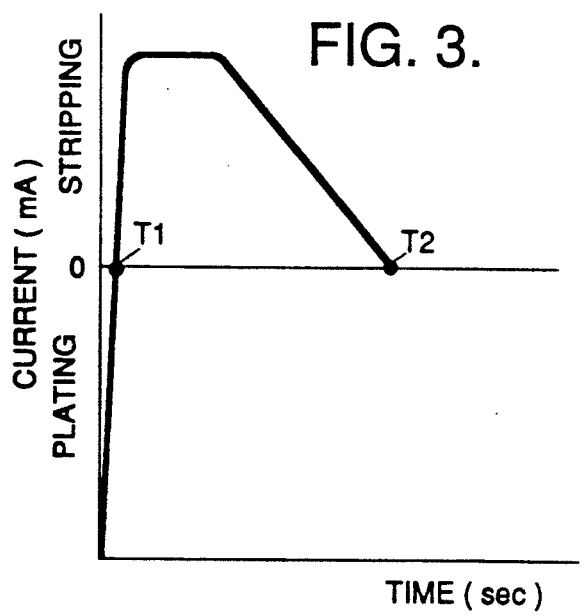
FIG. 3 is an illustration of an exemplary stripping signal response current produced in accordance with the present invention as applied to an acid cadmium plating bath containing multiple organic addition agents as trace constituents. The duration of the response current indicates the concentration level of one exemplary organic addition agent, Starter K.

The sensing electrode 10 positioned within the acid cadmium bath was pretreated at an anodic potential of about 3.0 volts, for a period of about 10 seconds. A dc pulse waveform with an amplitude of about $-2.0$ volts and a duration of about 100 ms was used to plate the pretreated electrode 10. The most rapidly adsorbed of the three organic addition agents is Starter K, and the above plating signal duration was less than the time required for Starter K to form a monolayer coverage of the electrode surface. A dc pulse signal with an amplitude of about 0.5 volts and a duration of about 1000 ms was then immediately applied to the plated electrode 10. This voltammetric stripping signal produced a response current which was monitored on display 6. An exemplary response current display is shown in FIG. 3 The time interval T2–T1 is proportional to the concentration level of the most rapidly adsorbed organic additive, Starter K. The method was found to provide an accurate indication of Starter K concentration within the acid cadmium bath. Measurements were repeatable over a wide range of concentration levels for all three organic addition agents. The results are shown in Table 1.

TABLE 1

| STARTER K (Vol. %) | Stripping Time As a Function of Addition Agent Concentration. | | |
|---|---|---|---|
| | BRIGHTENER KR (Vol. %) | STABILIZER (Vol. %) | STRIPPING TIME (ms) |
| 3.5 | 1.25 | 0.5 | 21 |
| 3.5 | 2.5 | 1.0 | 21 |
| 5.0 | 2.0 | 0.75 | 17 |
| 7.0 | 1.25 | 0.5 | 13 |
| 7.0 | 2.5 | 1.0 | 12 |

Although the above example relates to exemplary organic addition agents as trace constituents, this is by way of illustration and not limitation. The method can also be used to monitor many other types of trace constituents. Furthermore, although the above discussion is primarily directed to distinguishing the most rapidly adsorbed trace constituent, the method may also be used to distinguish the effects of trace constituents influencing the plating deposit which are not necessarily the most rapidly adsorbed in the bath. It will be understood by those skilled in the art that these and many other alternate implementations of the present invention are possible without deviating from the scope of the invention, which is limited only by the appended claims.

What is claimed is:

1. A method of selectively monitoring the concentration of an organic addition agent present in a plating bath solution containing multiple trace constituents and metal ions wherein said organic addition agent is more rapidly absorbed than said trace constituents, said method comprising the steps of:

providing at least one sensing electrode in contact with said solution;

applying a pretreatment signal of an amplitude and duration to said sensing electrode in contact with said solution in order to remove contaminants from said sensing electrode to provide a substantially contaminant-free electrode;

applying a plating signal of an amplitude and duration to said electrode, such that a portion of said metal ions from said solution form a plating on the surface of said electrode to form a plated electrode, and such that a portion of said organic addition agent is absorbed on said electrode surface;

applying a stripping signal of an amplitude and duration to said plated electrode, such that said plating on said surface of said plated electrode is removed, and further such that a stripping signal response current is produced, said stripping signal response current having signal characteristics responsive to said organic addition agent absorbed on said electrode surface; and monitoring said signal characteristics of said stripping response current;

wherein variations in said stripping response current characteristics provide an accurate indication of the concentration level of said organic addition agent.

2. The method of claim 1 wherein said pretreatment signal is a dc signal with an amplitude of about 2.5 to 3.5 volts and a duration of about to 5 to 15 seconds.

3. The method of claim 1 wherein said plating signal is a dc pulse signal with a potential which is cathodic to yield current densities of about 100 to 1000 ma/cm$^2$ and a duration of about 50 to 100 ms.

4. The method of claim 1 wherein said stripping signal is a dc pulse signal with a potential which is cathodic to strip the metal deposit over a duration of about 5 to 1000 ms.

5. The method of claim 1 wherein said monitored characteristic of said stripping signal response current is the time interval between the initial application of said stripping signal to said plated electrode and the time at which said stripping signal response current is substantially reduced to zero,, said time interval providing an accurate indication of the concentration of said particular trace constituent.

6. The method of claim 1 wherein said plating signal duration is less than the time required for said adsorbed particular trace constituent to form a monolayer saturating said electrode surface.

7. The method of claim 1 wherein said plating bath is an acid cadmium plating bath and further wherein said multiple trace constituents include Starter K, Brightener KR and Stabilizer.

8. The method of claim 7 wherein said selectively monitored particular trace constituent is Starter K.

9. The method of claim 8 wherein said pretreatment signal is a dc signal with an amplitude of about 3.0 volts and a duration of about 10 seconds.

10. The method of claim 8 wherein said plating signal is a dc pulse signal with an amplitude of about $-2$ volts and a duration of about 100 ms.

11. The method of claim 8 wherein said stripping signal is a dc pulse signal with an amplitude of about $+0.5$ volts and a duration of about 1000 ms.

* * * * *